United States Patent [19]

Carobbi et al.

[11] Patent Number: 5,003,061

[45] Date of Patent: Mar. 26, 1991

[54] METHOD FOR PREPARING HIGH-PURITY CRYSTALLINE LACTULOSE

[75] Inventors: Renato Carobbi, Pistoia; Franco Innocenti, Bagno a Ripoli, both of Italy

[73] Assignee: SIRAC Srl, Milan, Italy

[21] Appl. No.: 141,786

[22] Filed: Jan. 11, 1988

[30] Foreign Application Priority Data

Dec. 1, 1987 [IT] Italy .................................. 22848 A/87

[51] Int. Cl.$^5$ ........................... C07H 1/06; C13F 1/02
[52] U.S. Cl. ..................................... 536/127; 536/1.1; 536/4.1; 127/30; 127/46.1; 127/58
[58] Field of Search .................... 536/1.1, 4.1, 127; 127/30, 46.1, 58

[56] References Cited

U.S. PATENT DOCUMENTS

| | | | |
|---|---|---|---|
| 3,110,600 | 11/1963 | Bok | 536/1.1 |
| 3,546,206 | 12/1970 | Guth et al. | 127/30 |
| 3,562,012 | 2/1971 | Reinicke et al. | 536/1.1 |
| 3,816,174 | 6/1974 | Nagasawa et al. | 127/30 |
| 3,816,394 | 6/1974 | Nagasawa et al. | 536/124 |
| 4,142,916 | 3/1979 | Ogasa et al. | 127/63 |
| 4,264,763 | 4/1981 | Gasparotti | 536/1.1 |
| 4,273,922 | 6/1981 | Hicks | 127/46.1 |
| 4,536,221 | 8/1985 | Carobbi et al. | 536/127 |
| 4,555,271 | 11/1985 | Carobbi et al. | 127/46.2 |
| 4,605,646 | 8/1986 | Bernardi | 514/53 |
| 4,812,444 | 3/1989 | Mitsuhashi et al. | 514/53 |

FOREIGN PATENT DOCUMENTS

| | | |
|---|---|---|
| 57-102200 | 6/1982 | Japan . |
| 61-104800 | 5/1986 | Japan . |
| 1232554 | 5/1971 | United Kingdom . |
| 2031430 | 4/1980 | United Kingdom . |

OTHER PUBLICATIONS

Montgomery et al; J.A.C.S. 52:2101–2106, May 1930.
Oosten; Chemical Abstracts 67:73799k (1967).
Nitsch et al; Chemical Abstracts 84:150910v (1976).
Krol et al; Chemical Abstracts 90:40510f (1979).
Takahashi; Chemical Abstracts 105:135841g (1986).

*Primary Examiner*—Ronald W. Griffin
*Assistant Examiner*—Nancy S. Carson
*Attorney, Agent, or Firm*—Parkhurst, Wendel & Rossi

[57] ABSTRACT

A method for preparing high-purity crystalline lactulose and the product obtained by the method, which comprises crystallization from aqueous solutions at a temperature of 5°–40° C., the starting aqueous solution having a lactulose concentration of 50–80% w/w, a lactose concentration of less than 5% of the lactulose concentration by weight, a galactose concentration of less than 5% of the lactulose concentration by weight, and a concentration of other sugars of less than 4% of the lactulose concentration by weight.

4 Claims, No Drawings

METHOD FOR PREPARING HIGH-PURITY CRYSTALLINE LACTULOSE

FIELD OF THE INVENTION

This invention relates to a new method for preparing high-purity crystalline lactulose by crystallizing aqueous solutions which contain it and eliminating the secondary components during the crystallization stage, and to the crystalline lactulose obtained in this manner.

PRIOR ART

Lactulose, or 4-O-β-D-galactopyranosyl-D-fructofuranose, is a semisynthetic disaccharide used in the form of a syrup or crystalline product for its laxative effects, for its effectiveness in hepatic disfunctions and particularly in portosystemic encephalopathy, or as a sweetener.

Commercially available lactulose syrup is generally impure, containing variable quantities of other carbohydrates, particularly lactose and galactose.

A typical composition of currently available syrup is the following:

| | |
|---|---|
| lactulose | 50% by weight |
| galactose | 5-8% by weight |
| lactose | 3-5% by weight |
| other carbohydrates | 5-10% by weight | in which relatively large percentages of carbohydrates other than lactulose are present. These carbohydrates are also present, generally in lesser quantity, in currently commercially available crystalline lactulose.

Carbohydrates other than lactulose are undesirable in therapeutic applications for which lactulose is intended, and in particular for patients requiring a galactose-free diet and diabetic patients.

There is therefore a requirement for crystalline lactulose of higher purity, in particular with the greatest possible reduction in carbohydrates other than lactulose and with the absence of undesirable residual alcoholic solvent concentrations, which are present when lactulose is crystallized from alcoholic solutions.

The main currently known lactulose purification methods involve the use of alcoholic solvents, generally ethanol, together with complex procedures based on the extreme solubility of lactulose in an aqueous environment, or on various concentration processes by drying.

Crystalline lactulose obtained from alcoholic solvents is known to always contain a considerable percentage of solvent retained by the crystal, probably by the formation of hydrogen bonds between the sugar OH groups and the solvent OH groups, and it is never possible to eliminate the solvent residue even by prolonged drying.

One example of a process of purification by crystallization from ethanol is described in Italian patent No. 1,155,429.

The yield of such processes when calculated with respect to the lactulose contained in the starting syrup is particularly low.

In the present text the term "yield" indicates the amount of crystalline product obtained in a single step, as a weight percentage of the starting lactulose.

Thus, processes for obtaining crystalline lactulose from alcoholic solutions have the drawbacks of greater complication, lower yields and consequent higher cost, and a product from which the undesirable alcoholic solvent traces cannot be eliminated.

Again, processes involving concentration by direct drying of aqueous lactulose solutions, even if of high purity and whatever drying method is used (vacuum, lyophilization, spray drying), are known to lead to a very hygroscopic solid amorphous product or, as described in JP No. 61104800, to a solid containing crystalline lactulose which has to undergo further mixing and grinding before it can be used.

Thus none of the previously used methods has provided crystalline lactulose free both of impurities in the form of other undesirable carbohydrates and of residual concentrations of alcoholic solvent retained by the lactulose crystal.

Up to the present time it has been impossible in practice to directly obtain from aqueous solutions high-purity crystalline lactulose having the characteristics of the lactulose claimed in the present patent.

SUMMARY OF THE INVENTION

In accordance with the present invention we have now discovered a new industrially applicable lactulose purification process which obviates all these drawbacks and enables crystalline lactulose to be obtained in a particularly simple and economical manner with a degree of purity exceeding 98% by weight and practically free of carbohydrates other than lactulose, in particular lactose and galactose, from aqueous solutions which contain it in an impure state due to the presence of carbohydrates other than lactulose, and/or alcohols. If the process of the present invention is applied to lactulose crystallized from alcoholic solutions and then redissolved in water, the crystalline lactulose finally obtained is practically free of any trace of the alcoholic solvent used and thus has a degree of purity considerably higher than that obtainable by any process previously used.

The final yield of the process according to the invention varies according to the crystallization temperature, the crystallization time, the lactulose purity and the solution purity, and lies between 10 and 70%.

In its preferred embodiments, the yield varies from 55 to 70% as indicated hereinafter, and is therefore considerably greater than in all previously used methods, so making this process usable more economically on an industrial scale than previous processes.

The method of the present invention enables crystalline lactulose to be obtained from aqueous solutions which are impure because of the presence of carbohydrates other than lactulose and/or alcohols, and in particular from aqueous solutions having the following characteristics:

(a) lactulose concentration of 50–80% w/w and preferably 65–70% w/w in the aqueous solution;

(b) lactose concentration of less than 5% of the lactulose concentration by weight;

(c) galactose concentration of less than 5% of the lactulose concentration by weight;

(d) concentration of other carbohydrates of less than 4% of the lactulose concentration by weight;

(e) total concentration of carbohydrates other than lactulose not exceeding 6% of the lactulose concentration by weight.

The method according to the present invention is characterised by maintaining the crystallization conditions within precise critical values, and more specifically by simultaneously maintaining all the indicated parameters within the following defined critical values:

a. Crystallization temperature between 5° and 40° C., and preferably between 10° and 15° C.

b. Crystallization time between 10 and 60 hours, and preferably between 24 and 36 hours.

Outside these values an extremely low final process yield is obtained such that the process cannot be used industrially, it being sufficient for only one of these parameters to lie outside the range of values defined by the present invention for the final yield to be such as to make the process unusable industrially.

This process, which is described in detail in the examples, therefore not only enables crystalline lactulose to be obtained directly from sufficiently pure aqueous solutions, but also enables the residual solvent to be completely eliminated from crystalline lactulose obtained by conventional crystallization from alcoholic solvents such as methanol, ethanol and propanol.

The following examples are given as non-limiting illustration of the process according to the invention for purifying and crystallizing lactulose from aqueous solutions.

EXAMPLE 1

1000 kg of a lactulose solution having the following composition:

| lactulose | 50% |
|---|---|
| lactose | 0.7% |
| galactose | 0.9% |
| other sugars | 0.3% |
| water | to make up to 100% | are concentrated under vacuum to a lactulose concentration of 70%.

The concentrated solution is then cooled to 13° C. and 1 kg of crystalline lactulose is added.

The mixture is left under agitation for 24 hours maintaining the temperature at 13° C., after which the solid obtained, consisting of crystalline lactulose, is filtered off.

The solid is dried in an air oven at a temperature not exceeding 35°–40° C. to obtain 273 kg of crystalline lactulose with a purity exceeding 98% and a yield of 54.5%.

EXAMPLE 2

1000 kg of a lactulose solution having the following composition:

| lactulose | 50% |
|---|---|
| lactose | 0.7% |
| galactose | 0.9% |
| other sugars | 0.3% |
| water | to make up to 100% | are concentrated under vacuum to a lactulose concentration of 68%.

The concentrated solution is cooled to 35° C. after which 1 kg of crystalline lactulose is added.

Over a period of 20 hours the temperature is cooled to 15° C. while maintaining slow agitation, this temperature then being maintained for a further 16 hours.

By centrifuging, 373 kg of wet product (KF 17%) are obtained, equivalent to 309.5 kg of dry product, with a yield of 61.7% and a purity of 98.3%.

EXAMPLE 3

500 kg of crystalline lactulose (purity 98.7%) obtained by crystallization from ethanol, with a residual ethanol concentration of 5000 ppm, are dissolved in 2000 l of water.

The solution obtained is concentrated under vacuum to 68% of lactulose and its temperature allowed to reach 30°–35° C. spontaneously.

Crystallization is triggered by adding 800 g of crystalline lactulose.

The solution is then cooled to about 15° C. and kept at this temperature for 30 hours.

By centrifuging, 430 kg of wet product (KF 18%) are obtained, equivalent to 342.5 kg of dry product, with a yield of 68.5% and a purity exceeding 99%.

The residual ethanol content is reduced to less than 5 ppm.

We claim:

1. A method for preparing crystalline lactulose having less than 2% of carbohydrate other than lactulose and a purity exceeding 98% comprising:
   (a) adding a crystalline lactulose seed to an aqueous solution of lactulose having a lactulose concentration of from 50% to 80% w/w, a lactose concentration of less than 5% of the lactulose concentration by wt., a galactose concentration of less than 5% of the lactulose concentration by wt. and concentration of other carbohydrates of less than 4% of the lactulose concentration by wt.;
   (b) crystallizing said lactulose solution at a temperature between 5° and 40° C. and in a time between 10 and 60 hours; and
   (c) drying the obtained crystalline lactulose.

2. A method as claimed in claim 1, wherein the lactulose concentration in the aqueous solution is 65–70% w/w and the total concentration of carbohydrates other than lactulose does not exceed 6% of the lactulose concentration by weight.

3. The method of claim 1 wherein said lactulose solution crystallizing temperature is between 10° C. and 15° C. and said time is between 24 and 36 hours.

4. The method of claim 1 wherein the aqueous solution of lactulose is obtained by dissolving lactulose, which was previously crystallized from alcoholic solutions, in water.

* * * * *

UNITED STATES PATENT AND TRADEMARK OFFICE
CERTIFICATE OF CORRECTION

PATENT NO. : 5,003,061
DATED : March 26, 1991
INVENTOR(S) : Renato CAROBBI et al.

It is certified that error appears in the above-identified patent and that said Letters Patent is hereby corrected as shown below:

Title Page:
[73] Assignee: Please change "SIRAC Srl, Milan, Italy" to

--INALCO S.p.A., Milano, Italy--

Signed and Sealed this

Fifth Day of January, 1993

*Attest:*

DOUGLAS B. COMER

*Attesting Officer*     *Acting Commissioner of Patents and Trademarks*

REEXAMINATION CERTIFICATE (2940th)
United States Patent [19]
Carobbi et al.

[11] B1 5,003,061
[45] Certificate Issued Jul. 2, 1996

[54] METHOD FOR PREPARING HIGH-PURITY CRYSTALLINE LACTULOSE

[75] Inventors: Renato Carobbi, Pistoia; Franco Innocenti, Bagno a Ripoli, both of Italy

[73] Assignee: Inalco SpA, Milan, Italy

Reexamination Request:
No. 90/003,836, May 10, 1995

Reexamination Certificate for:
Patent No.: 5,003,061
Issued: Mar. 26, 1991
Appl. No.: 141,786
Filed: Jan. 11, 1988

Certificate of Correction issued Jan. 5, 1993.

[30] Foreign Application Priority Data

Dec. 1, 1987 [IT] Italy ..................................... 22848/87

[51] Int. Cl.$^6$ .................. C07H 1/06; C13F 1/02
[52] U.S. Cl. .................. 536/127; 536/1.1; 536/4.1; 536/123.13; 536/124; 127/30; 127/46.1; 127/58
[58] Field of Search .................. 536/123.13, 124, 536/1.1, 127, 4.1, 30; 127/46.1, 58

[56] References Cited

U.S. PATENT DOCUMENTS 4,536,221  8/1995  Carobbi .

FOREIGN PATENT DOCUMENTS 61-104800  5/1986  Japan .
2143826  2/1985  United Kingdom .

OTHER PUBLICATIONS

Nickerson, "By-products From Milk", Second Edition, edited by Byron H. Webb, Chapter 12, (1970).
Bucke, "Developments in Sweeteners–1)", edited by Hough et al, Chapter 2 (1979).
Van Hook, "Sugar Its Production, Technology, and Uses", pp. 39–42 and 128–132 (1949).
Bulletin of Japan Dairy Technical Association, vol. 22, No. 2, pp. 3–15 (1972)(English Translation of pertinent portions attached).
Pavia et al, "Introduction of Organic Laboratory Techniques A Contemporary Approach, Second Edition", pp. 486–488, (1982).
Kirk–Othmer Encyclopedia of Chemical Technology, 3rd Edition, vol. 7, pp. 243–285 (1979).

*Primary Examiner*—Gary L. Kunz

[57] ABSTRACT

A method for preparing high-purity crystalline lactulose and the product obtained by the method, which comprises crystallization from aqueous solutions at a temperature of 5°–40° C., the starting aqueous solution having a lactulose concentration of 50–80% w/w, a lactose concentration of less than 5% of the lactulose concentration by weight, a galactose concentration of less than 5% of the lactulose concentration by weight, and a concentration of other sugars of less than 4% of the lactulose concentration by weight.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2, 3 and 4, dependent on an amended claim, are determined to be patentable.

1. A method for preparing crystalline lactulose having less than 2% of carbohydrate other than lactulose and a purity exceeding 98% comprising:

(a) adding a crystalline lactulose seed to an aqueous solution of lactulose having a lactulose concentration of from 50% to 80% w/w, a lactose concentration of less than 5% of the lactulose concentration by wt., a galactose concentration of less than 5% of the lactulose concentration by wt. and concentration of other carbohydrates of less than 4% of the lactulose concentration by wt., *said aqueous solution containing water as the only solvent*;

(b) crystallizing said lactulose solution at a temperature between 5° and 40° C. and in a time between 10 and 60 hours; and (c) drying the obtained crystalline lactulose.

* * * * *